United States Patent
Batra et al.

(10) Patent No.: US 7,105,657 B2
(45) Date of Patent: Sep. 12, 2006

(54) COMPOSITIONS AND METHODS FOR INHIBITING PANCREATIC CANCER METASTASIS

(75) Inventors: Surinder K. Batra, Omaha, NE (US); Ajay P. Singh, Omaha, NE (US); Nicolas Moniaux, Omaha, NE (US)

(73) Assignee: Board of Regents of the University of Nebraska, Lincoln, NE (US)

( * ) Notice: Subject to any disclaimer, the term of this patent is extended or adjusted under 35 U.S.C. 154(b) by 500 days.

(21) Appl. No.: 10/291,151

(22) Filed: Nov. 8, 2002

(65) Prior Publication Data

US 2004/0091869 A1   May 13, 2004

(51) Int. Cl.
*C07H 21/04* (2006.01)
(52) U.S. Cl. .................... 536/24.5; 536/23.1
(58) Field of Classification Search ............... None
See application file for complete search history.

(56) References Cited

U.S. PATENT DOCUMENTS

| | | | | |
|---|---|---|---|---|
| 5,530,114 | A * | 6/1996 | Bennett et al. | 536/24.3 |
| 5,624,803 | A * | 4/1997 | Noonberg et al. | 435/6 |
| 5,981,279 | A * | 11/1999 | Weiss | 435/375 |
| 6,001,651 | A * | 12/1999 | Bennett et al. | 435/375 |
| 6,716,627 | B1 * | 4/2004 | Dobie | 435/375 |
| 2003/0077568 | A1 * | 4/2003 | Gish et al. | 435/4 |

OTHER PUBLICATIONS

Moniaux et al. (1999) Biochem. J. 338:325-333.*
Andrianifahanana, M., et al., "Mucin (Muc) gene expression in human pancreatic adenocarcinoma and chronic pancreatitis: A potential role of MUC4 as a tumor marker of diagnostic significance"; Clin. Cancer. Res., 7:4033-4040 (2001).
Balague, C., et al., "Altered Expression of MUC2, MUC4, and MUC5 mucin genes in pancreas tissues and cancer cell lines"; Gastroenterology 106:1054-1061 (1994).
Caldas, C., et al., "Detection of K-ras mutations in the stool of patients with pancreatic adenocarcinoma and pancreatic ductal hyperplasia" Cancer Res.; 54: 3568-3573 (1994).
Choudhury, A., et al., "MUC4 Mucin Expression in Human Pancreatic Tumors is Affected by Organ Environment: Possible Role of TGFbeta2"; Abstract, Br. J. Cancer, 90(3): 657-64 (2004).
Day, J.D., et. al., "Immunohistochemical evaluation of HER-2/neu oncogene expression in pancreatic adenocarcinoma and pancreatic intraepithelial neoplasms"; Hum. Pathol. 27: 119-124 (1996).
Dimagno, E.P., et. al., "AGA technical review on the epidemiology, diagnosis, and treatment of pancreatic ductal adenocarcinoma"; American Gastroenterological Association, Gastroenterology 117: 1464-1484 (1999).

Hameed, M., et. al., "Expression of p53 nucleophosphoprotein in in situ pancreatic ductal adenocarcinoma: an immunohistochemical analysis of 100 cases"; Lab. Invest. 70: 132A (1994).
Hollingsworth, M.A., et. al., "Expression of MUC1, MUC2, MUC3, and MUC4 mucin mRNAs in human pancreatic and intestinal tumor cell lines"; Int. J. Cancer 57: 198-203 (1994).
Khorrami, A.M., "Purification and characterization of a human pancreatic adenocarcinoma mucin"; J. Biochem. Jan; 131(1):21-9 (2002).
Komatsu, M., et al., "Muc4/sialomucin complex, an intramembrane modulator of ErbB2/HER2/Neu, potentiates primary tumor growth and suppresses apoptosis in a xenotransplanted tumor"; Oncogene 20(4): 461-470 (2001).
Komatsu, M., et al., "Potentiation of metastasis by cell surface sialomucin complex (rat MUC4), a multifunctional anti-adhesive glycoprotein"; Int. J. Cancer, 87:480-486 (2000).
Komatsu, M., et al., "Overexpression of sialomucin complex, a rat homologue of MUC4, inhibits tumor killing by lymphokine-activated killer cells"; Cancer Research, 59: 2229-2236 (1999).
Luttges, J., et. al., "The K-ras mutation pattern in pancreatic ductal adenocarcinoma usially is identical to that in associated normal hyperplastic, metaplastic ductal epithelium"; Cancer 85: 1703-1710 (1999).
Nollet, S., et. al., "Human mucin gene MUC4: Organization of its 5'-region and polymorphism of its central tandem repeat array"; Biochem. J. 15: 739-748 (1998).
Parker, S.L., et. al., "Cancer statistics, 1996"; Cancer J. Clin. 46:5-27 (1996).
Schwartz, M.J., et al., "MUC4 expression increases progressively in pancreatic intraepithelial neoplasia"; Am. J. Clin. Pathol., 117:791-796 (2002).
Tada, M., et. al., "Analysis of K-ras gene mutation in hyperplastic duct cells of the pancreas without pancreatic disease"; Gastroenterology 110: 227-231 (1996).
Walsh, M.D., et. al., "Expression of MUC2 epithelial mucin in breast carcinoma"; J. Clin. Pathol. 46: 922-925 (1993).
Warshaw, A.L., et. al., "Pancreatic carcinoma"; N. Engl. J. Med. 326: 455-465 (1992).
Wilentz, R.E., et. al., "Immunohistochemistry labeling for Dpc4 mirrors genetic status in pancreatic and peripancreatic adenocarcinomas: a new marker of DPC4 inactivation"; Am. J. Pathol. 156: 37-43 (2000).
Terris, B., et al., "Mucin gene expression in intraductal papillary-mucinous pancreatic tumours and related lesions"; J. Pathol. 197(5): 632-637 (2002).

\* cited by examiner

*Primary Examiner*—Andrew Wang
*Assistant Examiner*—Louis V. Wollenberger
(74) *Attorney, Agent, or Firm*—Dann Dorfman Herrell and Skillman; Kathleen D. Rigaut

(57) ABSTRACT

Methods are provided for the inhibition of metastasis of cancer cells expressing MUC4, metastatic pancreatic cancer cells.

18 Claims, 3 Drawing Sheets

COMPOSITIONS AND METHODS FOR INHIBITING PANCREATIC CANCER METASTASIS

STATEMENT OF GOVERNMENT RIGHT

Pursuant to 35 U.S.C. §202(c), it is acknowledged that the United States government has certain rights in the invention described herein, which was made in part with funds from the National Institutes of Health Grant No. CA78590.

FIELD OF THE INVENTION

This invention relates to the fields of molecular biology and oncology. More specifically, this invention provides compositions and methods for inhibiting the metastasis of MUC4 expressing cancer cells.

BACKGROUND OF THE INVENTION

Several publications and patent documents are referenced in this application by numerals in parentheses in order to more fully describe the state of the art to which this invention pertains. Full citations for these references are found at the end of the specification. The disclosure of each of these publications and documents is incorporated by reference herein.

Pancreatic adenocarcinoma (PA) belongs to a group of neoplasms which exhibit a relatively high level of incidence and poor prognosis (1). In the United States, PA is the fifth leading cause of cancer-related deaths and has the lowest 5-year survival rate of any cancer (2,3). In the year 2000, for example, an estimated 28,600 deaths will be ascribed to this type of cancer and approximately 28,600 new cases will be diagnosed.

PA has a median survival of 9–12 months and an overall 5-year survival rate of 3% for all stages. At the time of diagnosis, over four-fifths of patients with PA have clinically apparent metastatic disease. Among patients whose disease is considered to be resectable, 80% will die of recurrent tumor within 2 years. Accordingly, a need exists for early detection of pancreatic cancer and methods for treatment and/or prevention of the disease.

SUMMARY OF THE INVENTION

In accordance with the present invention, antisense molecules targeted to nucleic acids encoding MUC4 are provided. The antisense molecules of the invention specifically hybridize with nucleic acid molecules encoding MUC4 and inhibit the expression MUC4. In a preferred embodiment, the antisense molecules of the invention comprise the sequences of SEQ ID NO: 1 and SEQ ID NO: 2. The antisense molecules provided above may optionally comprise modified phosphodiester backbones which enhance in vivo stability. Phosphorothioates represent an exemplary modified phosphodiester backbone.

According to another aspect of the invention, a method is provided for inhibiting the in vivo expression of MUC4 in metastatic cancer cells. The method comprises contacting cancer cells or tissues in vivo with an antisense molecule of the invention so that expression of MUC4 is inhibited.

In yet a further embodiment of the present invention, a method is provided for inhibiting the growth and/or establishment of metastatic pancreatic cancer. The method comprises delivering an antisense molecule comprising the sequence of SEQ ID NO: 1 or SEQ ID NO: 2 to a patient which binds specifically to the nucleic acid molecule encoding MUC4 in an amount sufficient to inhibit expression of MUC4 in a pancreatic cancer cell.

In yet another embodiment of the invention, a pharmaceutical preparation is provided for treating metastatic pancreatic cancer. The pharmaceutical preparation includes an antisense oligonucleotide comprising the sequence of SEQ ID NO: 1 or SEQ ID NO: 2 in a biologically compatible medium. In yet another aspect, the pharmaceutical preparation may optionally comprise at least one targeting agent for improving delivery of the antisense molecule to pancreatic cancer cells (e.g., encapsulation of the preparation in an antibody-studded liposome). The pharmaceutical preparation of the invention may optionally further comprise at least one anti-cancer agent. Examples of such anti-cancer agents include, without limitation, cisplatin, gemcitabine, carboplatin, herceptinm, taxol, taxane derivatives, cyslophosphamide, methotrexate, vincristin, and etoposide.

In another aspect of the invention, antibodies immunologically specific for MUC4 are provided. Such antibodies may be monoclonal or polyclonal, and include recombinant, chimerized, humanized, antigen binding fragments of such antibodies, and anti-idiotypic antibodies. Methods for administration of such antibodies to patients to inhibit metastatic pancreatic cancer are also disclosed. Such antibodies may optionally be conjugated to a toxic molecule (e.g., ricin or diptheria toxin) to eradicate pancreatic cancer cells from the patient.

In a further aspect of the invention, kits for diagnosis or therapy are provided. An exemplary kit comprises a MUC4-antisense molecule in a biologicially acceptable carrier medium, at least one additional anti-cancer agent and optionally an antibody immunologically specific for MUC4. The kits may also include an excipient, a suitable container, and instructions for administration.

DETAILED DESCRIPTION OF THE INVENTION

Figure 1:
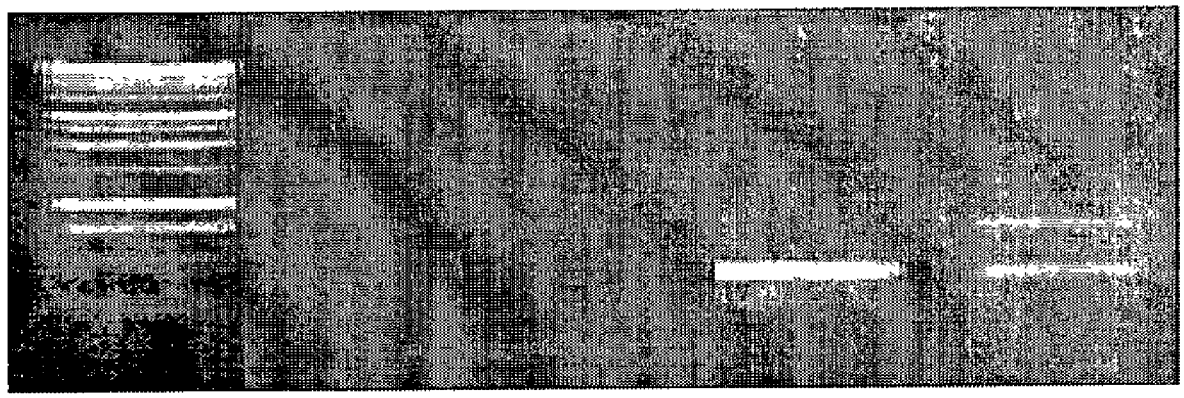
FIG. 1 is a gel showing the results of RT-PCR analysis of the CD18/HPAF cells and three selected clones [pcDNA3.1-C2 (mock transfected), pcDNA3.1-ES6 (sense transfected), and pcDNA3.1-EIAS19 (antisense transfected)] using vector specific primers.

Abnormal expression of MUC4 has been reported in various carcinomas. For example, increased expression of MUC4 mRNA species is observed in pancreatic carcinoma and cell lines, mammary carcinomas, non-small-cell lung cancers, and colon carcinomas (16–19). In accordance to the present invention, for the first time, it has been discovered that MUC4 provides a suitable target for the prevention or inhibition of cancer cell metastasis. More specifically, targeting MUC4 mRNA with antisense molecules or targeting MUC4 protein with anti-MUC4 antibodies or fragments thereof are capable of inhibiting metastasis of cancer cells that express MUC4. Such cancer cells include, but not limited to, pancreatic cancer cells, mammary cancer cells, non-small-cell lung cancer cells, and colon cancer cells.

The detailed description set forth below describes methods for practicing the present invention. Methods for selecting and preparing antisense nucleic acid molecules, antisense-encoding expression vectors, anti-MUC4 antibodies, and fragments thereof are provided, as well as methods for administering such compositions in vivo.

I. Definitions:

The following definitions are provided to facilitate an understanding of the present invention:

"Nucleic acid" or a "nucleic acid molecule" as used herein refers to any DNA or RNA molecule, either single or double stranded and, if single stranded, the molecule of its complementary sequence in either linear or circular form. In discussing nucleic acid molecules, a sequence or structure of a particular nucleic acid molecule may be described herein according to the normal convention of providing the sequence in the 5' to 3' direction. With reference to nucleic acids of the invention, the term "isolated nucleic acid" is sometimes used. This term, when applied to DNA, refers to a DNA molecule that is separated from sequences with which it is immediately contiguous in the naturally occurring genome of the organism in which it originated. For example, an "isolated nucleic acid" may comprise a DNA molecule inserted into a vector, such as a plasmid or virus vector, or integrated into the genomic DNA of a prokaryotic or eukaryotic cell or host organism.

When applied to RNA, the term "isolated nucleic acid" refers primarily to an RNA molecule encoded by an isolated DNA molecule as defined above. Alternatively, the term may refer to an RNA molecule that has been sufficiently separated from other nucleic acids with which it would be associated in its natural state (i.e., in cells or tissues). An isolated nucleic acid (either DNA or RNA) may further represent a molecule produced directly by biological or synthetic means and separated from other components present during its production.

With respect to single stranded nucleic acids, particularly oligonucleotides, the term "specifically hybridizing" refers to the association between two single-stranded nucleotide molecules of sufficiently complementary sequence to permit such hybridization under pre-determined conditions generally used in the art (sometimes termed "substantially complementary"). In particular, the term refers to hybridization of an oligonucleotide with a substantially complementary sequence contained within a single-stranded DNA molecule of the invention, to the substantial exclusion of hybridization of the oligonucleotide with single-stranded nucleic acids of non-complementary sequence. Appropriate conditions enabling specific hybridization of single stranded nucleic acid molecules of varying complementarity are well known in the art.

For instance, one common formula for calculating the stringency conditions required to achieve hybridization between nucleic acid molecules of a specified sequence homology is set forth below (Sambrook et al., 1989):

$T_m = 81.5°\ C. + 16.6\ \text{Log}\ [Na^+] + 0.41(\%\ G+C) - 0.63(\%\ \text{formamide}) - 600/\#bp$ in duplex As an illustration of the above formula, using [Na+]=[0.368] and 50% formamide, with GC content of 42% and an average probe size of 200 bases, the $T_m$ is 57° C. The $T_m$ of a DNA duplex decreases by 1–1.5° C. with every 1% decrease in homology. Thus, targets with greater than about 75% sequence identity would be observed using a hybridization temperature of 42° C.

The term "probe" as used herein refers to an oligonucleotide, polynucleotide or DNA molecule, whether occurring naturally as in a purified restriction enzyme digest or produced synthetically, which is capable of annealing with or specifically hybridizing to a nucleic acid with sequences complementary to the probe. A probe may be either single-stranded or double-stranded. The exact length of the probe will depend upon many factors, including temperature, source of probe and use of the method. For example, for diagnostic applications, depending on the complexity of the target sequence, the oligonucleotide probe typically contains 15–25 or more nucleotides, although it may contain fewer nucleotides. The probes herein are selected to be complementary to different strands of a particular target nucleic acid sequence. This means that the probes must be sufficiently complementary so as to be able to "specifically hybridize" or anneal with their respective target strands under a set of pre-determined conditions. Therefore, the probe sequence need not reflect the exact complementary sequence of the target. For example, a non-complementary nucleotide fragment may be attached to the 5' or 3' end of the probe, with the remainder of the probe sequence being complementary to the target strand. Alternatively, non-complementary bases or longer sequences can be interspersed into the probe, provided that the probe sequence has sufficient complementarity with the sequence of the target nucleic acid to anneal therewith specifically.

The term "primer" as used herein refers to a DNA oligonucleotide, either single-stranded or double-stranded, either derived from a biological system, generated by restriction enzyme digestion, or produced synthetically which, when placed in the proper environment, is able to functionally act as an initiator of template-dependent nucleic acid synthesis. When presented with an appropriate nucleic acid template, suitable nucleoside triphosphate precursors of nucleic acids, a polymerase enzyme, suitable cofactors and conditions such as a suitable temperature and pH, the primer may be extended at its 3' terminus by the addition of nucleotides by the action of a polymerase or similar activity to yield a primer extension product. The primer may vary in length depending on the particular conditions and requirement of the application. For example, in diagnostic applications, the oligonucleotide primer is typically 15–25 or more nucleotides in length. The primer must be of sufficient complementarity to the desired template to prime the synthesis of the desired extension product, that is, to be able anneal with the desired template strand in a manner sufficient to provide the 3' hydroxyl moiety of the primer in appropriate juxtaposition for use in the initiation of synthesis by a polymerase or similar enzyme. It is not required that the primer sequence represent an exact complement of the desired template. For example, a non-complementary nucleotide sequence may be attached to the 5' end of an otherwise complementary primer. Alternatively, non-complementary bases may be interspersed within the oligonucleotide primer sequence, provided that the primer sequence has sufficient complementarity with the sequence of the desired template strand to functionally provide a template-primer complex for the synthesis of the extension product.

Polymerase chain reaction (PCR) has been described in U.S. Pat. Nos. 4,683,195, 4,800,195, and 4,965,188, the entire disclosures of which are incorporated by reference herein. The terms "percent similarity", "percent identity" and "percent homology" when referring to a particular sequence are used as set forth in the University of Wisconsin GCG software program.

The term "functional" as used herein implies that the nucleic or amino acid sequence is functional for the recited assay or purpose.

The phrase "consisting essentially of" when referring to a particular nucleotide or amino acid means a sequence having the properties of a given SEQ ID NO. For example, when used in reference to an amino acid sequence, the phrase includes the sequence per se and molecular modifications that would not affect the basic and novel characteristics of the sequence.

A "replicon" is any genetic element, for example, a plasmid, cosmid, bacmid, phage or virus, that is capable of replication largely under its own control. A replicon may be either RNA or DNA and may be single or double stranded.

A "vector" is a replicon, such as a plasmid, cosmid, bacmid, phage or virus, to which another genetic sequence or element (either DNA or RNA) may be attached so as to bring about the replication of the attached sequence or element.

An "expression operon" refers to a nucleic acid segment that may possess transcriptional and translational control sequences, such as promoters, enhancers, translational start signals (e.g., ATG or AUG codons), polyadenylation signals, terminators, and the like, and which facilitate the expression of a polypeptide coding sequence in a host cell or organism.

The term "oligonucleotide," as used herein refers to sequences, primers and probes of the present invention, and is defined as a nucleic acid molecule comprised of two or more ribo- or deoxyribonucleotides, preferably more than three. The exact size of the oligonucleotide will depend on various factors and on the particular application and use of the oligonucleotide.

The term "antibody fragment" or "fragment thereof" refers to a portion or fragment of an intact antibody molecule, wherein the fragment retains antigen-binding function; i.e., F(ab')$_2$, Fab', Fab, Fv, single chain Fv ("scFv), Fd', and Fd fragments. Methods for producing the various fragments from monoclonal antibodies are well known to those skilled in the art (see, e.g., pluckthum, 1992, *Immunol. Rev.* 130:152–188).

The term "mammalian host" or "host" refers to a mouse or a human.

The term "overexpressing MUC4" refers to those cancerous cells wherein MUC4 are expressed in an elevated level compared to the level in normal cells.

II. Selection and Preparation of Antisense Nucleic Acid Molecules which Inhibit the Expression of MUC4

Antisense nucleic acids targeted to any known nucleotide sequence can be prepared by nucleotide synthesis according to standard methods. Synthesis of oligonucleotides via phosphoramidite chemistry is preferred, since it is an efficient method for preparing oligodeoxynucleotides, as well as being adapted to many commercial oligonucleotide synthesizers.

Selection of a suitable antisense sequence depends on knowledge of the nucleotide sequence of the target mRNA, or gene from which the mRNA is transcribed. The full length sequence of MUC4 is known (GenBank Accession No. AJ276359) In accordance with the present invention, antisense nucleic acid constructs #1 and #3 (described herein below; SEQ ID NOS: 1 and 2) target i) the junction between exon 1 and intron 1 of the MUC4 encoding nucleic acid and ii) sequences within exon 1 of MUC4.

Synthetic antisense oligonucleotides should be of sufficient length to hybridize to the target nucleotide sequence and exert the desired effect, i.e., blocking translation of an mRNA molecule. It is also possible that such antisense molecules may be delivered to a patient in a plasmid or nucleic acid vector. Using standard methodology known to those skilled in the art, it is possible to maintain the antisense RNA-encoding DNA in any convenient cloning vector (see Ausubel et al., eds. *Current Protocols in Molecular Biology*, John Wiley and Sons, Inc., (1995)). In one embodiment, clones are maintained in a plasmid cloning/expression vector, such as pCEP4 (Invitrogen), which is propagated in a suitable host cell.

Various genetic regulatory control elements may be incorporated into antisense RNA-encoding expression vectors to facilitate propagation in both eucaryotic and procaryotic cells. Different promoters may be utilized to drive expression of the MUC4 antisense sequences, such as the cytomegalovirus immediate early promoter which promotes a high level of expression of downstream sequences. Polyadenylation signal sequences are also utilized to promote mRNA stability. Sequences may be used in the invention include, but are not limited to, bovine growth hormone polyadenylation signal sequences or thymidine kinase polyadenylation signal sequences. Antibiotic resistance markers are also included in these vectors to enable selection of transformed cells. These may include, for example, genes that confer hygromycin, neomycin or ampicillin resistance. According to one embodiment of the present invention, antisense nucleic acid molecules are cloned into palsmid pcDNA3.1/zeo(+) behind the cytomegalovirus promoter.

Antisense nucleic acids such as those described above are highly susceptible to degradation by assorted nucleases. Moreover, such molecules may be unable to enter cells because of insufficient membrane permeability. For these reasons, practitioners skilled in the art generally synthesize oligonucleotides that are modified in various ways to increase stability and membrane permeability. The use of modified antisense oligonucleotides is preferred in the present invention. The term "antisense oligonucleotide analog" refers to such modified oligonucleotides, as discussed hereinbelow.

Several methods of modifying oligodeoxyribo-nucleotides are known in the art. For example, methylphosphonate oligonucleotide analogs may be synthesized wherein the negative charge on the internucleotide phosphate bridge is eliminated by replacing the negatively charged phosphate oxygen with a methyl group. See Uhlmann et al., Chemical Review, 90: 544–584 (1990). Another common modification, which is utilized in an embodiment of the present invention, is the synthesis of oligodeoxyribonucleotide phosphorothioates. In these analogs, one of the phosphate oxygen atoms not involved in the phosphate bridge is replaced by a sulphur atom, resulting in the negative charge being distributed asymmetrically and located mainly on the sulphur atoms. When compared to unmodified oligonucleotides, oligonucleotide phosphorothioates are improved with respect to stability to nucleases, retention of solubility in water and stability to base-catalyzed hydrolysis. See Uhlmann et al., supra at 548–50; Cohen, J. S. (ed.) *Oligodeoxynucleotides: Antisense Inhibitors of Gene Expression*, CRC Press, Inc., Boca Raton, Fla. (1989).

Other modifications of oligodeoxyribonucleotides to produce stable, membrane permeable oligonucleotide analogs are commonly known in the art. For a review of such methods, see generally, Uhlmann et al., supra, and Cohen, supra which also describe methods for synthesis of such molecules. In addition, modified oligoribonucleotides may be utilized in the present invention. However, oligodeoxyribonucleotides are preferred due to their enhanced stability, ease of manufacture and the variety of methods available for analog synthesis.

Still other modifications of the oligonucleotides may include coupling sequences that code for RNase H to the antisense oligonucleotide. This enzyme (RNase H) will then hydrolyze the hybrid formed by the oligonucleotide and the specific targeted mRNA. Alkylating derivatives of oligonucleotides and derivatives containing lipophilic groups can also be used. Alkylating derivatives form covalent bonds with the mRNA, thereby inhibiting their ability to translate proteins. Lipophilic derivatives of oligonucleotides will increase their membrane permeability, thus enhancing penetration into tissue. Besides targeting the mRNAs, other antisense molecules can target the DNA, forming triple DNA helixes (DNA triplexes). Another strategy is to administer sense DNA strands which will bind to specific regulator cis or trans active protein elements on the DNA molecule.

Deoxynucleotide dithioates (phosphorodithioate DNA) may also be utilized in this invention. These compounds which have nucleoside-$OPS_2O$ nucleoside linkages, are phosphorus achiral, anionic and are similar to natural DNA. They form duplexes with unmodified complementary DNA. They also activate RNase H and are resistant to nucleases, making them potentially useful as therapeutic agents. One such compound has been shown to inhibit HIV-1 reverse transcriptase (Caruthers et al., INSERM/NIH Conference on Antisense Oligonucleotides and Ribonuclease H, Arcachon, France 1992).

III. Administration of Oligonucleotides and/or Plasmid Vectors Producing RNA Molecules Antisense MUC4 encoding nucleic acids and/or vectors as described herein are generally administered to a patient as a pharmaceutical preparation. The term "patient" as used herein refers to human or animal subjects.

The pharmaceutical preparation comprising the antisense oligonucleotides or plasmid vectors encoding antisense RNA of the invention are conveniently formulated for administration with an acceptable medium such as water, buffered saline, ethanol, polyol (for example, glycerol, propylene glycol, liquid polyethylene glycol and the like), dimethyl sulfoxide (DMSO), oils, detergents, suspending agents or suitable mixtures thereof. The concentration of antisense oligonucleotides in the chosen medium will depend on the hydrophobic or hydrophilic nature of the medium, as well as the length and other properties of the antisense molecule. Solubility limits may be easily determined by one skilled in the art.

As used herein, "biologically acceptable medium" includes any and all solvents, dispersion media and the like which may be appropriate for the desired route of administration of the pharmaceutical preparation, as exemplified in the preceding paragraph. The use of such media for pharmaceutically active substances is known in the art. Except insofar as any conventional media or agent is incompatible with the antisense molecules to be administered, its use in the pharmaceutical preparation is contemplated.

Selection of a suitable pharmaceutical preparation depends upon the method of administration chosen. For example, antisense nucleic acids may be administered by direct injection into cancerous tissue. In this instance, a pharmaceutical preparation comprises the antisense molecule dispersed in a medium that is compatible with the cancerous tissue.

Nucleic acids antisense to MUC4 mRNAs may be administered parenterally by intravenous injection into the blood stream, or by subcutaneous, intramuscular or intraperitoneal injection. Pharmaceutical preparations for parenteral injection are commonly known in the art. If parenteral injection is selected as a method for administering the antisense oligonucleotides, steps must be taken to ensure that sufficient amounts of the molecules reach their target cells to exert a biological effect. The lipophilicity of the antisense molecules, or the pharmaceutical preparation in which they are delivered may have to be increased so that the molecules can arrive at their target locations. Furthermore, the antisense molecules may have to be delivered in a cell-targeted carrier so that sufficient numbers of molecules will reach the target cells. Methods for increasing the lipophilicity of a molecule are known in the art, and include the addition of lipophilic groups to the antisense oligonucleotides. Two specific antisense carriers, phosphorothioate and methylphosphonate oligonucleotide analogs, become widely dispersed in living tissues following intravenous injection. For example, experiments in mice, which provided a detailed analysis of the pharmacokinetics, biodistribution and stability of oligonucleotide phosphorothioates showed a widespread distribution of phosphorothioate-modified oligodeoxynucleotides in most tissues for up to 48 hours. Significant amounts were found in brain following intraperitoneal or intravenous administration. Agrawal et al., Proc. Natl. Acad. Sci. USA, 88: 7595–99 (1991). In another study, methylphosphonate oligonucleotides were injected into mouse tail veins and found to achieve a reasonably uniform distribution in mouse tissue. See Uhlmann et al., supra at 577, citing Miller et al., Anti-Cancer Drug Design, 2: 117 (1987).

Several techniques have been used to increase the stability, cellular uptake and biodistribution of oligonucleotides. Antisense oligonucleotides of the present invention may be encapsulated in a lipophilic, targeted carrier, such as a liposome. One technique is to use as a carrier for the oligonucleotide a liposomal preparation containing the cationic lipid N-[1-(2,3-dioleyloxy)propyl]-N,N,N-trimethyl ammonium chloride (D OT MA; lipofectin). This has been found to increase by about 1000 fold the potency of the antisense oligonucleotide ISIS 1570, which hybridizes to the AUG translation initiation codon of human intracellular adhesion molecule-1. Bennett et al., Mol Pharmacol., 41: 1023–1033 (1992). Phosphorothioates have been particularly useful for increasing the biodistribution and stability of oligodeoxynucleotides in mice as described above. Loading phosphorothioate oligonucleotides into liposomes, particularly pH sensitive liposomes, to increase their cellular uptake has also been used with some success. Loke et al., Curr. Topics Microbiol. Immunol., 141: 282–289 (1988); Connor and Huang, Cancer Res., 46: 3431–3435 (1986).

Additional means by which antisense oligonucleotides may be administered include oral or rectal administration into the gastrointestinal tract, as well as intranasal or ophthalmic administration.

A pharmaceutical preparation of the invention may be formulated in dosage unit form for ease of administration and uniformity of dosage. Dosage unit form, as used herein, refers to a physically discrete unit of the pharmaceutical preparation appropriate for the patient undergoing treatment. Each dosage should contain a quantity of active ingredient calculated to produce the desired effect in association with the selected pharmaceutical carrier. Procedures for determining the appropriate dosage unit are well known to those skilled in the art.

Dosage units may be proportionately increased or decreased based on the weight of the patient. Appropriate concentrations for alleviation of a particular pathological condition may be determined by dosage concentration curve calculations, as known in the art.

In accordance with the present invention, the appropriate dosage unit for the administration of antisense oligonucleotides directed to nucleic acids encoding MUC4 may be determined by evaluating the toxicity of the antisense oligonucleotides in animal models. Various concentrations of antisense pharmaceutical preparations may be administered to mice with transplanted human tumors, and the minimal and maximal dosages may be determined based on the results of significant reduction of tumor size and side effects as a result of the treatment. Appropriate dosage unit may also be determined by assessing the efficacy of the antisense oligonucleotide treatment in combination with other standard anti-cancer drugs. The dosage units of antisense oligonucleotide may be determined individually in combination with each anti-cancer treatment according to efficacies of inhibiting cancer cell metastasis.

The pharmaceutical preparation comprising the antisense oligonucleotides may be administered at appropriate intervals, for example, twice a day until the pathological symptoms are reduced or alleviated, after which the dosage may be reduced to a maintenance level. The appropriate interval in a particular case would normally depend on the condition of the patient.

While the above discussion refers to the delivery of antisense oligonucleotides, it will be apparent to those skilled in the art that the methods described would also be suitable for the delivery of the vector constructs encoding MUC4 mRNA-specific antisense molecules.

In accordance with the present invention, the pharmaceutical preparation of MUC4 antisense nucleic acid molecules may further comprises at least one anti-cancer agent. Suitable anti-cancer agents include, but are not limited to, cisplatin, gemcitabine, carboplatin, herceptinm, taxol, taxane derivatives, cyslophosphamide, methotrexate, vincristin, and etoposide.

IV. Preparation of anti-MUC4 Antibodies and Fragments Thereof

The present invention also provides antibodies capable of immunospecifically binding to MUC4. Polyclonal antibodies directed toward human MUC4 protein may be prepared according to standard methods. In a preferred embodiment, monoclonal antibodies are prepared, which react immunospecifically with the various epitopes of the MUC4 protein. Monoclonal antibodies have been prepared according to general methods of Köhler and Milstein, following standard protocols. Specifically, various peptides (representing various portions of the MUC4 protein were synthesized and conjugated to the KLH protein as an immunogen and evaluated for their immunogenecity in rabbits. Ten weeks after immunization, rabbit sera demonstrated the presence of high titer antibodies (82, 982; 47,338; and 31,108 units) that reacted specifically with MUC4 tandem repeat peptide, (STGDTTPLPVTDTSSV; SEQ ID NO: 3), MUC4 α (ATYRPPQPAWMFGD; SEQ ID NO: 4) and MUC4 β (GARFSYFLNSAEALP; SEQ ID NO: 5) peptides. These polyclonal antibodies showed specific reactivity in immunohistochemistry assays to MUC4 expressing cells.

Mice in three groups were immunized by repeated intraperitoneal injection of the above mentioned peptide antigens. Once an appropriate antibody response was determined by reciprocal 50% endpoint titers in excess of 5,000 vs antigen, the animal was given a final booster injection 3–4 days prior to splenectomy and exsanguination. The lymphocytes were isolated from the spleens and were fused with NS-1 myeloma cells. Those hybridomas producing anti-MUC4 antibodies of interest were selected by screening for specific antibody binding to the MUC4 peptide of interest and a lack of binding to irrelevant control antigens. A panel of monoclonal antibodies immunologically specific for MUC-4 have been obtained in this manner.

Purified MUC4 protein, or fragments thereof, may be used to produce polyclonal or monoclonal antibodies of the present invention. Recombinant techniques enable expression of fusion proteins containing part or all of MUC4 protein. The full length protein or fragments of the protein may be used to advantage to generate an array of monoclonal antibodies specific for various epitopes of MUC4 protein, thereby providing even greater efficiency in inhibiting metastasis of pancreatic cancer cells.

Also within the scope of the present invention are fragments of anti-MUC4 antibodies. Such antibody fragments can be obtained, for example, by proteolytic hydrolysis of the antibody. Antibody fragments can be obtained by pepsin or papain digestion of whole antibodies by conventional methods. As an illustration, antibody fragments can be produced by enzymatic cleavage of antibodies with pepsin to provide a 5S fragment denoted F(ab')$_2$. This fragment can be further cleaved using a thiol reducing agent to produce 3.5S Fab' monovalent fragments. Optionally, the cleavage reaction can be performed using a blocking group for the sulfhydryl groups that result from cleavage of disulfide linkages. As an alternative, an enzymatic cleavage using pepsin produces two monovalent Fab fragments and an Fc fragment directly. These methods are described, for example, by Goldenberg, U.S. Pat. No. 4,331,647, Nisonoff et al., *Arch Biochem. Biophys.* 89:230 (1960), Porter, *Biochem. J.* 73:119 (1959), Edelman et al., in *Methods in Enzymology* Vol. 1, page 422 (Academic Press 1967), and by Coligan at pages 2.8.1–2.8.10 and 2.10.–2.10.4.

Other methods of cleaving antibodies, such as separation of heavy chains to form monovalent light-heavy chain fragments, further cleavage of fragments, or other enzymatic, chemical or genetic techniques may also be used, so long as the fragments bind to the antigen that is recognized by the intact antibody.

For example, Fv fragments comprise an association of $V_H$ and $V_L$ chains. This association can be noncovalent, as described by Inbar et al., *Proc. Nat'l Acad. Sci. USA* 69:2659 (1972). Alternatively, the variable chains can be linked by an intermolecular disulfide bond or cross-linked by chemicals such as glutaraldehyde (see, for example, Sandhu, *Crit. Rev. Biotech.* 12:437 (1992)).

The Fv fragments may comprise $V_H$ and $V_L$ chains which are connected by a peptide linker. These single-chain antigen binding proteins (scFv) are prepared by constructing a structural gene comprising DNA sequences encoding the $V_H$ and $V_L$ domains which are connected by an oligonucleotide. The structural gene is inserted into an expression vector which is subsequently introduced into a host cell, such as *E. coli*. The recombinant host cells synthesize a single polypeptide chain with a linker peptide bridging the two V domains. Methods for producing scFvs are described, for example, by Whitlow et al., *Methods: A Companion to Methods in Enzymology* 2:97 (1991) (also see, Bird et al., *Science* 242:423 (1988), Ladner et al., U.S. Pat. No. 4,946,778, Pack et al., *Bio/Technology* 11:1271 (1993), and Sandhu, supra).

As an illustration, a scFV can be obtained by exposing lymphocytes to MUC4 polypeptide in vitro, and selecting antibody display libraries in phage or similar vectors (for instance, through use of immobilized or labeled MUC4 protein or peptide). Genes encoding polypeptides having potential MUC4 polypeptide binding domains can be obtained by screening random peptide libraries displayed on phage (phage display) or on bacteria, such as *E. coli*. Nucleotide sequences encoding the polypeptides can be obtained in a number of ways, such as through random mutagenesis and random polynucleotide synthesis. These random peptide display libraries can be used to screen for peptides which interact with a known target which can be a protein or polypeptide, such as a ligand or receptor, a biological or synthetic macromolecule, or organic or inorganic substances. Techniques for creating and screening such random peptide display libraries are known in the art (Ladner et al., U.S. Pat. No. 5,223,409, Ladner et al., U.S. Pat. No. 4,946,778, Ladner et al., U.S. Pat. No. 5,403,484, Ladner et al., U.S. Pat. No. 5,571,698, and Kay et al., *Phage Display of Peptides and Proteins* (Academic Press, Inc. 1996)) and random peptide display libraries and kits for screening such libraries are available commercially, for instance from CLONTECH Laboratories, Inc. (Palo Alto, Calif.), Invitrogen Inc. (San Diego, Calif.), New England Biolabs, Inc. (Beverly, Mass.), and Pharmacia LKB Biotechnology Inc. (Piscataway, N.J.). Random peptide display libraries can be screened using the MUC4 gene sequences to identify proteins which bind to MUC4.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells (see, for example, Larrick et al., *Methods: A Companion to Methods in Enzymology* 2:106 (1991), Courtenay-Luck, "Genetic Manipulation of Monoclonal Antibodies," in *Monoclonal Antibodies: Production, Engineering and Clinical Application*, Ritter et al. (eds.), page 166 (Cambridge University Press 1995), and Ward et al., "Genetic Manipulation and Expression of Antibodies," in *Monoclonal Antibodies: Principles and Applications*, Birch et al., (eds.), page 137 (Wiley-Liss, Inc. 1995)).

Alternatively, an anti-MUC4 antibody may be derived from a "humanized" monoclonal antibody. Humanized forms of non-human (e.g., murine) antibodies are chimeric molecules of immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. Humanized antibodies include human immunoglobulins (recipient antibody) in which residues form a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., *Nature*, 321:522–525 (1986); Riechmann et al., *Nature*, 332:323–329 (1988); and Presta, *Curr. Op. Struct. Biol.*, 2:593–596 (1992)].

Methods for humanizing non-human antibodies are well known in the art. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers [Jones et al., *Nature*, 321:522–525 (1986); Riechmann et al., *Nature*, 332:323–327 (1988); Verhoeyen et al., *Science*, 239:1534–1536 (1988)], by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, *J. Mol. Biol.*, 227:381 (1991); Marks et al., *J. Mol. Biol.*, 2:581 (1991)]. The techniques of Cole et al. and Boemer et al. are also available for the preparation of human monoclonal antibodies (Cole et al., *Monoclonal Antibodies and Cancer Therapy*, Alan R. Liss, p. 77 (1985) and Boerner et al., *J. Immunol.*, 1471):86–95 (1991)]. Similarly, human antibodies can be made by introducing of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., *Bio/Technology* 10, 779–783 (1992); Lonberg et al., *Nature* 368 856–859 (1994); Morrison, *Nature* 368. 812–13 (1994); Fishwild et al., *Nature Biotechnology* 14, 84551 (1996); Neuberger, *Nature Biotechnology* 14, 826 (1996); Lonberg and Huszar, *Intern. Rev. Immunol.* 13 65–93 (1995).

Additionally, the anti-MUC4 antibodies or functional fragments thereof may be conjugated to toxic molecules to enhance tumor cell killing. Such toxic molecules include, without limitation, radio-nuclides, ricin and diptheria toxin.

II. Administration of Anti-MUC4 Antibodies or Fragments Thereof

The anti-MUC4 antibodies or fragments thereof are generally administered to a patient as a pharmaceutical preparation.

The pharmaceutical preparation comprising the anti-MUC4 antibodies or fragments thereof of the invention are conveniently formulated for administration with a acceptable medium such as water, buffered saline, ethanol, polyol (for example, glycerol, propylene glycol, liquid polyethylene glycol and the like), dimethyl sulfoxide (DMSO), oils, detergents, suspending agents or suitable mixtures thereof. The concentration of the anti-MUC4 antibodies or fragments thereof in the chosen medium will depend on the hydrophobic or hydrophilic nature of the medium, as well as the other properties of the anti-MUC4 antibodies or fragments thereof. Solubility limits may be easily determined by one skilled in the art.

As used herein, "biologically acceptable medium" includes any and all solvents, dispersion media and the like which may be appropriate for the desired route of administration of the pharmaceutical preparation, as exemplified in the preceding paragraph. The use of such media for pharmaceutically active substances is known in the art. Except insofar as any conventional media or agent is incompatible with the anti-MUC4 antibodies or fragments thereof to be administered, its use in the pharmaceutical preparation is contemplated.

Conventional passive immunization methods will be employed when administering the anti-MUC4 antibodies or fragments thereof of the invention. In a preferred embodiment, anti-MUC4 antibodies or fragments thereof will be infused intravenously into the patient. For treatment of certain medical disorders, steps must be taken to ensure that sufficient amounts of the molecules reach their target cells to exert a biological effect. The lipophilicity of the molecules, or the pharmaceutical preparation in which they are delivered may have to be increased so that the molecules can arrive at their target locations.

The anti-MUC4 antibodies or fragments thereof that are the subject of the present invention can be incorporated into a recombinant molecule or conjugated to a carrier such as polyethylene glycol. In addition, the anti-MUC4 antibodies or fragments thereof can be bound to carriers capable of causing the transfer across cell membranes. Carriers of this type include but not limited to those described by Cruikshank et al. in the *Journal of Acquired Immune Deficiency Syndromes and Human Retrovirology*, March 1997.

The pharmaceutical preparation is formulated in dosage unit form for ease of administration and uniformity of dosage. Dosage unit form, as used herein, refers to a physically discrete unit of the pharmaceutical preparation appropriate for the patient undergoing treatment. Each dosage should contain a quantity of active ingredient calculated to produce the desired effect in association with the selected pharmaceutical carrier. Procedures for determining the appropriate dosage unit are well known to those skilled in the art.

The pharmaceutical preparation comprising the anti-MUC4 antibodies or fragments thereof may be administered at appropriate intervals. The appropriate interval in a particular case would normally depend on the condition and the pathogenic state sought to be treated in the patient.

In accordance with the present invention, the pharmaceutical preparation of anti-MUC4 antibodies or fragments thereof may further comprise at least one anti-cancer agent. Suitable anti-cancer agents include, but are not limited to, cisplatin, gemcitabine, carboplatin, herceptinm, taxol, taxane derivatives, cyslophosphamide, methotrexate, vincristin, and etoposide.

The following examples provide illustrative methods of practicing the instant invention, and are not intended to limit the scope of the invention in any way.

EXAMPLE

I. Material and Methods

Construction of Plasmids Expressing MUC4 Antisense RNA: Two partial-length MUC4 DNA fragments, EcoRI__51688—BamHI__52286 (SEQ ID NO: 1) of human chromosome 3 sequence (Genbank accession No. AC025282) and EcoRI__390—BamHI__689 (SEQ ID NO: 2) of human mucin gene MUC4 (Genbank accession No. AJ000281), were obtained through PCR amplification using DNA template from S1243 MUC4 clone. The fragment EcoRI__51688—BamHI__52286 (SEQ ID NO: 1) covered 598 bp region from Exon 1 and Intron 1, while fragment EcoRI__390—BamHI__689 (SEQ ID NO: 2) contained a 300 bp stretch from exon 1 only. The two fragments were cloned in antisense orientations behind the cytomegalovirus promoter of the pcDNA3.1/zeo(+) vector from Invitrogen (San Diego, Calif., U.S.A.) by standard recombination techniques. The fragment EcoRI__390—BamHI__689 (SEQ ID NO: 2) was also cloned in sense orientation to serve as control. The resulting three constructs were designated pcDNA3-ES (sense), pcDNA3.1-EAS (exon antisense), and pcDNA3.1-EIAS (exon-intron antisense). The insertion of construct was analyzed by RT-PCR using vector specific primers and the orientation of the DNA inserts was verified by sequencing of the recombinants.

Cell Culture and Transfection Procedure: CD18/HPAF cells were cultured in DMEM:Ham's F12 (1:1) supplemented with 10% fetal calf serum and antibiotics. The cultures were incubated in a humidified atmosphere at 37° C. with 5% $CO_2$. The culture medium for transfected cells with zeocine-resistance reporter gene was supplemented with 200 µg/ml zeocin. The sense and antisense constructs along with the empty vector control pcDNA3.1/zeo were transfected in CD18/HPAF cells by lipofection using Lipofectamine (Invitrogen), following the manufacturer's protocol. Cells were selected in the medium containing 200 µg/ml zeocin. 20 drug-resistant ($zeo^+$) clones (three from empty vector, five each from sense and exon-antisense and seven from exon-intron antisense constructions transfected) were picked from different plates and studied after expansion.

Immunoblot Assay: CD18/HPAF and derived cell lines were processed for protein extraction and western blotting using standard procedures. Briefly, the cells were washed twice in PBS and scraped in RIPA buffer (100 mM Tris, 5 mM EDTA, 5% NP40; pH 8.0) containing protease inhibitors (1 mM phenyl-methyl sulphonyl fluoride, 1 µg/ml aprotinin, 1 µg/ml leupeptin) and kept at 4° C. for atleast 30 min. Cell lysates were passed through the needle syringe or alternatively, passed through one freeze thaw cycle to disrupt the cell membranes. Cell lysates were centrifuged at 14,000 rpm for 30 min at 4° C. and supernatants were collected. Protein concentrations were analyzed using BIO-RAD D/C protein estimation kit. SDS-agarose (2%) and SDS-PAGE (7.5%) was performed using 10 mg protein samples under reducing conditions for MUC4 and phosphoglycerol kinase (PGK), respectively. Resolved proteins were transferred on to the PVDF membrane. After quick washing in PBS (phosphate buffered saline), membranes were blocked in 5% nonfat dry milk in PBS for at least 2 hr and then incubated in anti-human MUC4 mouse monoclonal antibody (diluted in 1% nonfat dry milk in PBS) for 2 hr at room temperature. For PGK, membranes were incubated in anti-human PGK rabbit polyclonal antibody (Santa Cruz Biotechnology) antibodies for 2 hr at room temperature. The membranes were washed (6×10 min) in TBST (Tris buffered saline containing 0.05% Tween-20) at room temperature and then probed with 1:2000 diluted horseradish peroxidase-conjugated goat anti-mouse and anti rabbit secondary antibodies (Amarsham Biosciences Buckinghamshire, UK) for MUC4 and PGK, respectively for 1 hr at room temperature and washed 3×10 min with TBST. The signal was detected with ECL Chemiluminescence Kit (Amarsham Biosciences, Buckinghamshire, UK).

Confocal Immunofluorescent Microscopy: Cells were grown at low density on sterilized cover slips for 20 hours. Cells were washed with 0.1 M HEPES containing Hanks buffer, and fixed in ice-cold methanol at −20° C. for two minutes. Blocking was done in 10% goat serum containing 0.05% Tween-20 for at least 30 minutes followed by incubation with the anti-MUC4 monoclonal antibodies (20 µg/ml) in phosphate buffered saline (PBS), for 90 minutes at room temperature. Cells were washed 4×5 minutes with PBS containing 0.05% Tween-20 and then incubated with FITC-conjugated goat anti-mouse secondary antibodies for 60 minutes. Cells were washed twice and mounted on glass slides in anti-fade Vectashield mounting medium. Immunostaining was observed under ZEISS confocal laser scanning microscope.

Growth Rate: Cells ($10^4$ cells/3 ml of medium) were seeded in each well of a six-well plate and allowed to grow for different times. The trypsin-treated cells were counted on a haemocytometer or using a Coulter counter. Cell lines expressing the sense and antisense-MUC4 RNA segments, cells transfected with the empty vector, and the parental CD18/HPAF cell line were studied. Growth assays were determined by cell enumeration in triplicate for each cell line on every day of culture up to the seventh day.

Tumorigenicity Assay: To assess tumorigenic capacity, the anti-MUC4 transfected cells were orthotopically implanted in to baize nude mice at a concentration of $5×10^6$ cells/100 ml of normal saline. Tumor growth was assessed by the daily weighing and palpitation of each animal. The mice were housed in a controlled-environment animal facility and allowed free access to food and water. All the mice were sacrificed $21^{st}$ day after tumor cell implantation. Data were recorded on tumor volume, tumor weight, and number of metastatic lesions present on lung, liver, diaphragm, colon and lymph nodes (Table 1)

II. Results

Figure 2:
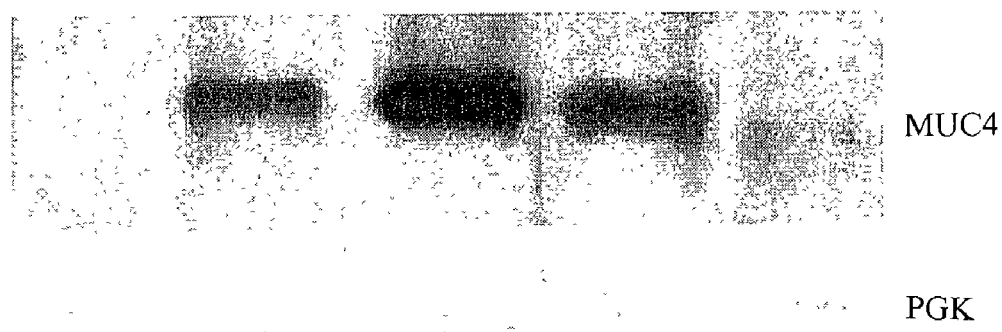
FIGS. 2A and 2B are a western blot and a graph showing MUC4 expression levels in CD18/HPAF and its derived sublines: pcDNA3.1-C2 (mock transfected), pcDNA3.1-ES6 (sense transfected), and pcDNA3.1-EIAS19 (antisense transfected); Panc1 was used as negative control. 10 µg protein samples were subjected to polyacrylamide gel electrophoresis on 2% SDS-agarose gel under reducing condition and resolved proteins were transferred to PVDF membrane for probing with anti-MUC4 monoclonal antibody. Phosphoglycerol kinase (PGK) was used as an internal control. The clone pcDNA3.1-EIAS19 shows 50–80% downregulation of MUC4 expression compared to CD18/HPAF, mock transfected and sense transfected controls.
Figure 2:
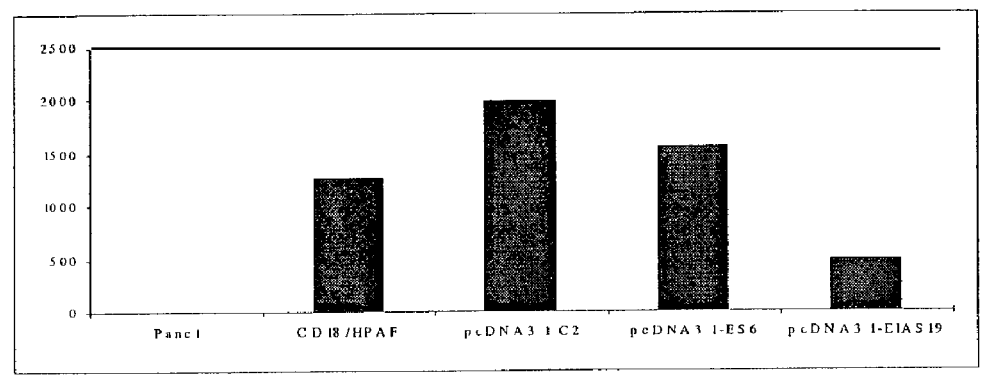

Selection of Stable Clones: CD18/HPAF pancreatic adenocarcinoma cells growing in vitro have been transfected by lipofection, with partial length cDNA constructions expressing two short antisense RNA segment, and one sense RNA segment under control of a strong CMV promoter and with the empty vector (pcDNA3.1-Zeo). After transfection, 20 different cell clones were selected upon growing the cells in zeocin containing media (three (3) from empty vector, five (5) each from sense and exon-antisense and seven (7) from exon-intron-antisense constructions transfected). The insertion of the gene construct and expression of the insert was determined by RT-PCR using the vector specific PCR primers (FIG. 1). MUC4 expression levels were examined via western blotting procedure (FIGS. 2A and 2B). Clone pcDNA3.1-EIAS-19, which showed up to 50–80% down-regulation of MUC4 protein synthesis, was further confirmed for reduced cellular expression of MUC4 by confocal immunofluorescent microscopy.

Figure 3:
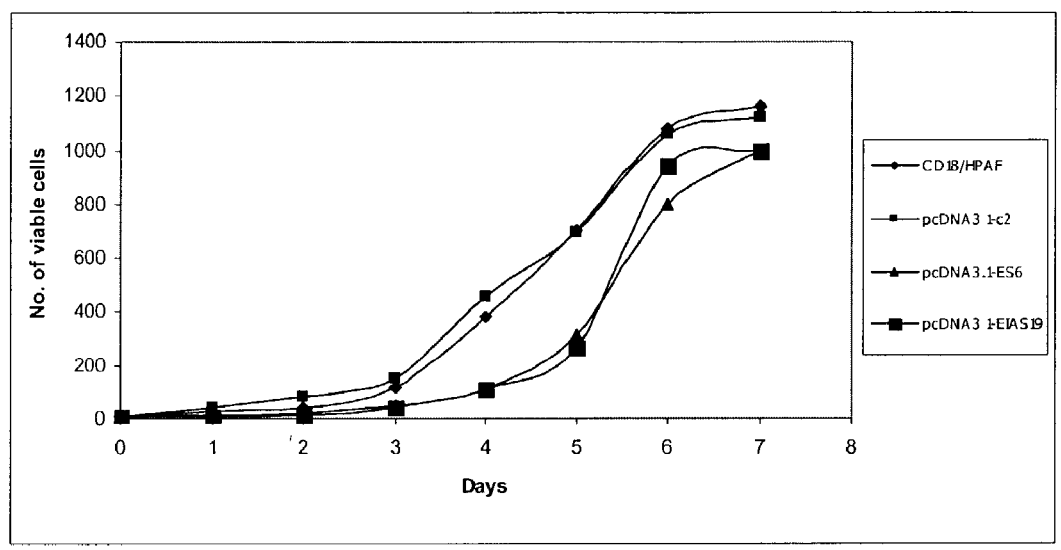
FIG. 3 is a graph showing the growth kinetics of CD18/HPAF, pcDNA3.1-C2 (mock transfected), pcDNA3.1-ES6 (sense transfected), and pcDNA3.1-EIAS19 (antisense transfected) cells. The transfected clone with the antisense-MUC4 cDNA segment (pcDNA3.1-EIAS-19) shows a decrease in growth rate compared to CD18/HPAF and empty vector (pcDNA3.1-C2) controls, while both sense (pcDNA3.1-ES-6) and antisense (pcDNA3.1-EIAS-19) clones shows similar growth properties.

Growth Characteristics and Morphology of the MUC4-Antisense-RNA Expressing cells: Cell-proliferation rates were determined for parental CD18/HPAF and its derived selected cell lines by cell enumeration in a Coulter counter or by haemocytometer (FIG. 3). The transfected clone with the antisense-MUC4 cDNA segment (pcDNA3.1-EIAS-19) showed a decrease in growth rate compared to CD18/HPAF and empty vector (pcDNA3.1-C2) controls. However, both sense (pcDNA3.1-ES-6) and antisense (pcDNA3.1-EIAS-19) clones showed similar growth properties. Further more, the antisense RNA expressing clones displayed a remarkable change in morphology, compared with control cell lines (data not shown): cells became polygonal and formed adherent clumps, in contrast with the random growth pattern of the controls.

Tumorigenicity: Tumorigenicity data is reported in Table 1. Five mice each were injected orthotopically with $5×10^6$ cell to assess the growth and metastatic potential of antisense RNA expressing clone (pcDNA3.1-EIAS-19) and the control cell lines. No significant differences in tumor weight and volume were recorded among the mice injected with antisense RNA expressing clone (reduced MUC4 protein expression) and other control cell lines. However, in antisense clone, only one mice showed metastatic lesions in diaphragm, compared to several lymph node metastatic lesions in others accompanied by metastases of liver and diaphragm in few cases. These data clearly demonstrates that inhibition of MUC4 expression markedly blocks tumor metastasis of pancreatic adenocarcinoma.

TABLE 1

Growth Characteristics and Metastatic Potential

| Metastasis | 1 | 2 | 3 | 4 | 5 | Average | Std. Dev. |
|---|---|---|---|---|---|---|---|
| CD18/HPAF | | | | | | | |
| Liver | — | — | — | — | — | — | |
| Lung | — | — | — | — | — | — | |
| Lymph node | 4 | 4 | — | 2 | 3 | | |
| Spleen | — | — | — | — | — | — | |
| Diaphragm | + | + | — | — | + | | |
| Pancreas (wt in gm) | 2 7 | 2 5 | 1 3 | 1 4 | 2 5 | 2 08 | 0.6013319 |
| Pancreas (vol – mm³) | 25 × 1 45 × 1.6 = 5890 | 1 × 1.5 × 2 5 = 3750 | 1 2 × 0 9 × 1 5 = 1620 | 1 2 × 0 9 × 1 6 = 1728 | 2 5 × 1 15 × 1 0 = 2875 | 3172 6 | 1753.8283 |
| C2-(injected-Jul. 17, 2002, sacrificed-Aug. 7, 2002) | | | | | | | |
| Liver | — | — | — | — | | | |
| Lung | — | — | — | — | | | |
| Lymph node | 4 | 4 | 3 | 4 | | | |
| Spleen | — | — | — | — | | | |

TABLE 1-continued

Growth Characteristics and Metastatic Potential

| Metastasis | 1 | 2 | 3 | 4 | 5 | Average | Std. Dev. |
|---|---|---|---|---|---|---|---|
| Diaphragm | — | — | — | + | | | |
| Pancreas (wt in gm) | 2 4 | 2 | 1.3 | 1 6 | | 182 | 0.4787136 |
| Pancreas (vol – mm³) | 2 1 × 1 8 × 0 8 = 3024 | 1 6 × 1 6 × 89 = 2278 | 1 × 1 37 × 1.5 = 2055 | 1 × 1.25 × 1 93 = 2406 | | 2440 75 | 415 00151 |
| C6 + (injected-Jul. 16, 2002, sacrificed-Aug. 7, 2002) | | | | | | | |
| Liver | +(1–2 tiny) | — | — | — | — | | |
| Lung | — | — | — | — | — | | |
| Lymph node | 4 | 7 | 5 | 2 | 5 | | |
| Spleen | — | — | — | — | — | | |
| Diaphragm | + | — | — | — | — | | |
| Pancreas (wt in gm) | 2 1 | 2 7 | 1 8 | 2.6 | 1 56 | 2 152 | 0 442285 |
| Pancreas (vol – mm³) | 1.25 × 1.5 × 2 = 3750 | 2 5 × 1.5 × 1 5 = 5625 | 1 75 × 1 75 × 1 = 3063 | 2 × 1.75 × 1 5 = 5250 | 2 × 1.25 × 1 0 = 2500 | 4037 6 | 1358 9081 |
| E119(injected-Jul. 16, 2002, sacrificed-Aug. 7, 2002) | | | | | | | |
| Liver | — | — | — | — | | | |
| Lung | — | — | — | — | | | |
| Lymph node | — | — | — | — | | | |
| Spleen | — | — | — | — | | | |
| Diaphragm | — | — | — | + | | | |
| Pancreas (wt in gm) | 3.1 | 1.75 | 1.8 | 0 8 | | 1.8625 | 0.9446119 |
| Pancreas (vol – mm³) | 2.35 × 1.75 × 1 75 = 7197 | 1 5 × 1.5 × 1.13 = 2531 | 1.15 × 1.13 × 1 73 = 2242 | 0.98 × 0 98 × 1 2 = 1165 | | 3283 75 | 2674.229 |

REFERENCES

1. Warshaw A L, Fernandez-del C C. Pancreatic carcinoma. *N Engl J Med* 1992; 326:455–465.

2. DiMagno E P, Reber H A, Tempero M A. AGA technical review on the epidemiology, diagnosis, and treatment of pancreatic ductal adenocarcinoma. American Gastroenterological Association. *Gastroenterology* 1999; 117: 1464–1484.

3. Parker S L, Tong T, Bolden S, Wingo P A. *Cancer statistics,* 1996. CA Cancer J Clin 1996; 46:5–27.

4. Day J D, DiGiuseppe J A, Yeo C J, et. al., Immunohistochemical evaluation of HER-2/neu oncogene expression in pancreatic adenocarcinoma and pancreatic intraepithelial neoplasms, *Hum Pathol* 1996; 27:119–124.

5. Tada M, Ohashi M, Shiratori Y, et. al., Analysis of K-ras gene mutation in hyperplastic duct cells of the pancreas without pancreatic disease, *Gastroenterology* 1996; 110: 227–231.

6. Caldas C, Hahn S A, Hruban R H, et. al., Detection of K-ras mutations in the stool of patients with pancreatic adenocarcinoma and pancreatic ductal hyperplasia, *Cancer Res* 1994; 54:3568–3573.

7. Khorrami A M, Purification and characterization of a human pancreatic adenocarcinoma mucin, *J Biochem* (Tokyo) 2002 January; 131 (1):21–9.

8. Hameed M, Marrero A M, Conlon K C, et. al., Expression of p53 nucleophosphoprotein in in situ pancreatic ductal adenocarcinoma: an immunohistochemical analysis of 100 cases, *Lab. Invest* 1994; 70:132A.

9. Wilentz R E, Su G H, Dai J L et. al., Immunohistochemistry labeling for Dpc4 mirrors genetic status in pancreatic and peripancreatic adenocarcinomas: a new marker of DPC4 inactivation, *Am J Pathol* 2000; 156: 37–43.

10. Luttges J, Schlehe B. Menke M A, et al, The K-ras mutation pattern in pancreateic ductal adenocarcinoma usially is identical to that in associated normal hyperplastic, metaplastic ductal epithelium, *Cancer* 1999; 85:1703–1710.

11. Balagué C, Gambús G, Carrato C, et. al., Altered Expression of MUC2, MUC4, and MUC5 mucin genes in pancreas tissues and cancer cell lines, *Gastroenterology* 1994; 106:1054–1061.

12. Andrianifahanana M, Moniaux N, Ringel J, et. al., MUCin (Muc) gene expression in human pancreatic adenocarcinoma and chronic pancreatitis: a potential role of MUC4 as a tumor marker of diagnostic significance, *Proceedings of the AACR* 2001; 42:1727

13. Andrianifahanana M. Monlaux N., Schmied B. M., Rigel J., Friess H., Hollingsworth M., Buchler M. W., Aubert J. P., and Batra S. K. Mucin (MUC) Gene Expression in Human Pancreatic Adenocarcinoma and Chronic Pancreatitis: a Potential Role of MUC4 as a Tumor Marker of Diagnostic Significance, *Clin Cancer Res.* 2001; 7:4033–4040.

14. Swart M. J., Batra S. K., Varshney G. C., Hollingsworth M. A., Yeo C. J., Cameron J. L., Wilentz R. E., Hruban R. H., and Argani P., MUC4 Expression Increases Progressively in Pancreatic Intraepithelial Neoplasia (PanIN), *Am J clin Pathol* 2002; 117:791–796.

15. Choudhury, A., Monlaux N., Ulrigh, A. B., Schmied, B. M., Standop, J., Pour, P. M., Gendler S., Hollingsworth M. A., Aubert, J. P., and Batra, S. K., Regulation of MUC4 mucin expression in human pancreatic adenocarcinoma by the host microenvironment, *Clin Cancer Res.*, revised submitted, 2002.

16. Balague C, Gambus G, Carrato C, Porchet N, Aubert J P, Kim Y S, Real F X., Altered expression of MUC2, MUC4, and MUC5 mucin genes in pancreas tissues and cancer cell lines, *Gastroenterology* 1994 April; 106 (4): 1054–61.

17. Hollingsworth M A, Strawhecker J M, Caffrey T C, Mack D R, Expression of MUC1, MUC2, MUC3 and MUC4 mucin mRNAs in human pancreatic and intestinal tumor cell lines, *Int J Cancer* 1994 Apr. 15; 57 (2):198–203.

18. Walsh M D, McGuckin M A, Devine P L, Hohn B G, Wright R G, Expression of MUC2 epithelial mucin in breast carcinoma, *J Clin Pathol* 1993 October; 46 (10):922–5.

19. Nollet S, Moniaux N, Maury J, Petitprez D, Degand P, Laine A, Porchet N, Aubert J P, Human mucin gene MUC4: organization of its 5'-region and polymorphism of its central tandem repeat array, *Biochem J* 1998 Jun. 15; 332 (Pt 3):739–48.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. An antisense nucleic acid molecule targeted to a nucleic acid molecule encoding human MUC4, wherein said antisense nucleic acid molecule is the complement of SEQ ID NO: 2.

2. The antisense nucleic acid molecule of claim 1, which is a DNA molecule.

3. The antisense nucleic acid molecule of claim 1, which is an RNA molecule.

4. The antisense nucleic acid of claim 1, which comprises at least one modified internucleoside linkage.

5. The antisense nucleic acid of claim 4, wherein said modified internucleoside linkage is a phosphorothioate linkage.

6. The antisense nucleic acid of claim 1, which comprises at least one modified sugar moiety.

7. The antisense nucleic acid of claim 6, wherein said modified sugar moiety is a 2'-o-methyloxymethyl sugar moiety.

8. The antisense of nucleic acid molecule claim 1, which comprises at least one modified base.

9. The antisense nucleic acid molecule of claim 8, wherein said modified base is a 5-methylcytosine.

10. A vector comprising a DNA which encodes the antisense nucleic acid molecule of claim 1.

11. A pharmaceutical preparation for inhibiting metastasis of cancer cells expressing MUC4, comprising the antisense nucleic acid molecule of claim 1 in a biologically compatible medium.

12. The pharmaceutical preparation of claim 11, wherein said antisense nucleic acid molecule comprises a modifications selected from the group consisting of a base, sugar, and lincage modification.

13. The pharmaceutical preparation of claim 11, further comprising at least one targeting agent for improving delivery of said antisense nucleic acid molecule to said cancer cells.

14. The pharmaceutical preparation of claim 13, wherein said at least one targeting agent comprises lipid.

15. The pharmaceutical preparation of claim 14, wherein said antisense nucleic acid molecule is encapsulated in an antibody-studded lipid vesicle.

16. The pharmaceutical preparation of claim 11, further comprising at least one additional anti-cancer agent.

17. The pharmaceutical preparation of claim 16, wherein said anti-cancer agent is selected from the group consisting of cisplatin, gemcitabine, carboplatin, herceptin, taxol, taxane derivatives, cyclophosphamide, methotrexate, vincristin, and etoposide.

18. A pharmaceutical preparation for inhibiting metastasis of cancer cells expressing MUC4, comprising the vector of claim 10 in a biologically compatible medium.

* * * * *

SEQUENCE LISTING

<160> NUMBER OF SEQ ID NOS: 5

<210> SEQ ID NO 1
<211> LENGTH: 619
<212> TYPE: DNA
<213> ORGANISM: Homo sapiens

<400> SEQUENCE: 1

```
cctgagggga cgggctcacg tctgctcctc acactgcagc tgctgggccg tggagcttcc      60
ccagggagcc aggggacactt ttgccgcagc catgaagggg gcacgctgga ggagggtccc    120
ctgggtgtcc ctgagctgcc tgtgtctctg cctccttccg catgtggtcc caggtaagtg    180
atggagacag cagatgaggc tggctgcggg gagcacttgg gggaggtggg agctgtcaga    240
gaaagaggtc cggggagaca gagagagaga gagagagaat aggggaaagg gagacagcga    300
agaggaagag aaggagaga aaaagaggga gagggaaagg agaaagagat gaatgggaca    360
acatgggggg aaggtggaga gagacccaga gagggaaaga agaggaagag aagagggaga    420
gagaaagaag agtggaggcc gtgcgcggtg gctcatgcct gtaatcccag cactttcgga    480
ggccaaggca ggagatcacc tgaggtcagg agttcgagac cagcctggcc gacatggtga    540
aaccccgtct ctactaaata tacaaaaatt agccggtcgt ggtgggcccc acctgtaatt    600
ccagctactc aggagtctg                                                  619
```

<210> SEQ ID NO 2
<211> LENGTH: 300
<212> TYPE: DNA
<213> ORGANISM: Homo sapiens

<400> SEQUENCE: 2

```
tctgctcctc acactgcagc tgctgggccg tggagcttcc ccagggagcc aggggacactt     60
ttgccgcagc catgaagggg gcacgctgga ggagggtccc ctgggtgtcc ctgagctgcc    120
tgtgtctctg cctccttccg catgtggtcc caggaaccac agaggacaca ttaataactg    180
gaagtaaaac tcctgcccca gtcacctcaa caggctcaac aacagcgaca ctagagggac    240
aatcaactgc agcttcttca aggacctcta atcaggacat atcagcttca tctcagaacc    300
```

<210> SEQ ID NO 3
<211> LENGTH: 16
<212> TYPE: PRT
<213> ORGANISM: Homo sapiens

<400> SEQUENCE: 3

Ser Thr Gly Asp Thr Thr Pro Leu Pro Val Thr Asp Thr Ser Ser Val
1               5                   10                  15

<210> SEQ ID NO 4
<211> LENGTH: 14
<212> TYPE: PRT
<213> ORGANISM: Homo sapiens

```
<400> SEQUENCE: 4

Ala Thr Tyr Arg Pro Pro Gln Pro Ala Trp Met Phe Gly Asp
1               5                   10

<210> SEQ ID NO 5
<211> LENGTH: 15
<212> TYPE: PRT
<213> ORGANISM: Homo sapiens

<400> SEQUENCE: 5

Gly Ala Arg Phe Ser Tyr Phe Leu Asn Ser Ala Glu Ala Leu Pro
1               5                   10                  15
```